(12) United States Patent
Chen et al.

(10) Patent No.: US 12,222,284 B2
(45) Date of Patent: Feb. 11, 2025

(54) METHOD FOR QUICKLY MEASURING CONTENT POLYCYCLIC AROMATIC HYDROCARBON IN CARBON BLACK

(71) Applicant: LINYUAN ADVANCED MATERIALS TECHNOLOGY CO., LTD., Kaohsiung (TW)

(72) Inventors: Hong-Zhang Chen, Kaohsiung (TW); Jheng-Guang Li, Kaohsiung (TW)

(73) Assignee: Linyuan Advanced Materials Technology Co., Ltd., Kaohsiung (TW)

( * ) Notice: Subject to any disclaimer, the term of this patent is extended or adjusted under 35 U.S.C. 154(b) by 0 days.

(21) Appl. No.: 17/715,382

(22) Filed: Apr. 7, 2022

(65) Prior Publication Data

US 2022/0326146 A1 Oct. 13, 2022

(30) Foreign Application Priority Data

Apr. 9, 2021 (TW) .................................. 110112877

(51) Int. Cl.
| | | |
|---|---|---|
| *G01N 21/33* | (2006.01) | |
| *A61B 5/0215* | (2006.01) | |
| *A61B 6/58* | (2024.01) | |
| *G01N 21/31* | (2006.01) | |

(52) U.S. Cl.
CPC ......... *G01N 21/33* (2013.01); *A61B 5/02156* (2013.01); *A61B 6/582* (2013.01); *G01N 2021/3125* (2013.01)

(58) Field of Classification Search
CPC ........... G01N 21/33; G01N 2021/3125; G01N 21/3151; G01N 2021/3155
See application file for complete search history.

(56) References Cited

U.S. PATENT DOCUMENTS

| | | | |
|---|---|---|---|
| 2008/0159947 A1* | 7/2008 | Yurovskaya | C09C 1/48 |
| | | | 423/449.1 |
| 2015/0089997 A1* | 4/2015 | Nema | G01N 30/06 |
| | | | 73/23.4 |

OTHER PUBLICATIONS

Dost, Kenan, and Cevat İdeli. "Determination of Polycyclic Aromatic Hydrocarbons in Edible Oils and Barbecued Food by HPLC/UV-Vis Detection." Food Chemistry, vol. 133, No. 1, 2012, pp. 193-199., https://doi.org/10.1016/j.foodchem.2012.01.001 (Year: 2012).*

(Continued)

*Primary Examiner* — Jennifer Wecker
(74) *Attorney, Agent, or Firm* — Cermak & McGowan LLP; Shelly Guest Cermak

(57) ABSTRACT

The present invention provides a method for measuring a content of a polycyclic aromatic hydrocarbon in a carbon black, comprising the following steps: extracting a carbon black to be measured using an organic solvent to obtain a sample to be tested; testing the sample to be tested by ultraviolet-visible spectrometer to obtain an absorbance; and using the absorbance and a calibration curve to obtain a content of a polycyclic aromatic hydrocarbon in the sample to be tested, wherein the calibration curve shows relationship between the absorbance of the polycyclic aromatic hydrocarbon and the content of the polycyclic aromatic hydrocarbon. The measurement method of the present invention benefits reduction of detection time.

14 Claims, 1 Drawing Sheet

(56) References Cited

OTHER PUBLICATIONS

Giger, Walter, and Blumer, Max "Polycyclic Aromatic Hydrocarbons in the Environment. Isolation and Characterization by Chromatography, Visible, Ultraviolet, and Mass Spectrometry." Analytical Chemistry, vol. 46, No. 12, 1974, pp. 1663-1671., https://doi.org/10.1021/ac60348a036 (Year: 1974).*

* cited by examiner

METHOD FOR QUICKLY MEASURING CONTENT POLYCYCLIC AROMATIC HYDROCARBON IN CARBON BLACK

This application claims priority under 35 U.S.C. § 119 to Taiwanese Patent Application No. 110112877, filed Apr. 9, 2021, the entirety of which is incorporated by reference herein.

BACKGROUND OF THE INVENTION

Field of the Invention

The present invention relates to a method for measuring a content of a polycyclic aromatic hydrocarbon in carbon black, which can be used to preliminarily estimate the total amount of the polycyclic aromatic hydrocarbon in carbon black, so that suitable carbon black can be quickly screened out.

Description of the Prior Art

Polycyclic aromatic hydrocarbons, abbreviated as PAHs or PAH, contain more than 100 compounds. Most polycyclic aromatic hydrocarbons have carcinogenic toxicity, therefore, polycyclic aromatic hydrocarbons are regarded as extremely serious pollutants. As a result, various countries have increasingly strict restrictions on the content of PAHs in products.

PAHs exist in carbon black products due to the adsorption characteristics of carbon black and the manufacturing conditions. In view of rising environmental awareness or related regulations, carbon black products nowadays are often required to have low PAHs, that is, the total content of 15 PAHs must be less than 50 ppm, or even less than 10 ppm.

The traditional measurement of PAHs content in carbon black is carried out by using gas chromatography-mass spectrometry (GC-MS), but GC-MS is a valuable instrument and has low popularity. As a result, if the content of PAHs in carbon black is needed to be measured, it is often required to be tested by a specific unit. In this way, it takes at least 2 to 3 working days to get the measurement results, which is not only time-consuming, but also not conducive to the monitoring of PAHs content on the production line.

SUMMARY OF THE INVENTION

In view of the above technical problems, an object of the present invention is to provide a novel method for measuring the content of PAHs in carbon black. More particularly, the object of the present invention is to provide a method for quickly measuring the content of PAHs in carbon black.

To achieve the above object, the present invention provides a method for measuring a content of a polycyclic aromatic hydrocarbon in carbon black, which comprises the following steps: extracting a carbon black to be measured using an organic solvent to obtain a sample to be tested; testing the sample to be tested by a ultraviolet-visible spectrometer to obtain an absorbance; and using the absorbance and a calibration curve to obtain a content of a polycyclic aromatic hydrocarbon in the sample to be tested, wherein the calibration curve shows a relationship between the absorbance of the polycyclic aromatic hydrocarbon and the content of the polycyclic aromatic hydrocarbon, wherein the polycyclic aromatic hydrocarbon is soluble in the organic solvent.

Preferably, the organic solvent is toluene, cyclohexane or a mixture thereof.

Preferably, the absorbance is tested at a wavelength of 200 nm to 500 nm. More preferably, the absorbance is tested at a wavelength of 290 nm to 500 nm.

Preferably, the calibration curve is corrected by linear regression.

Preferably, the polycyclic aromatic hydrocarbon includes at least one selected from the group consisting of benzo[a]pyrene, benzo[e]pyrene, benzo[a]anthracene, benzo[b]fluoranthene, benzo[j]fluoranthene, benzo[k]fluoranthene, chrysene, dibenzo[a,h]anthracene, benzo[g,h,i]perylene, indeno[1,2,3-cd]pyrene, anthracene, fluoranthene, phenanthrene, pyrene, naphthalene, acenaphthylene, acenaphthene, fluorine, 5-methylchrysene, perylene and benzo[ghi]fluoranthene.

Preferably, the calibration curve takes the absorbance of the polycyclic aromatic hydrocarbon as the data on the vertical axis and the content of the polycyclic aromatic hydrocarbon as the data on the horizontal axis.

The present invention further provides a method for measuring a content of a polycyclic aromatic hydrocarbon in carbon black, which comprises the following steps: extracting a carbon black to be measured using an organic solvent to obtain a sample to be tested; testing the sample to be tested by a ultraviolet-visible spectrometer to obtain an absorbance; using the absorbance and a calibration curve to obtain a content of a first polycyclic aromatic hydrocarbon in the sample to be tested, wherein the calibration curve shows a relationship between the absorbance of the first polycyclic aromatic hydrocarbon and the content of the first polycyclic aromatic hydrocarbon; and using the content of the first polycyclic aromatic hydrocarbon and a regression curve to obtain a content of a polycyclic aromatic hydrocarbon in the sample to be tested, wherein the first polycyclic aromatic hydrocarbon is a part of the polycyclic aromatic hydrocarbon, and the regression curve shows a relationship between the content of the first polycyclic aromatic hydrocarbon and the content of the polycyclic aromatic hydrocarbon, wherein the first polycyclic aromatic hydrocarbon and the polycyclic aromatic hydrocarbon are soluble in the organic solvent.

Preferably, the organic solvent is toluene, cyclohexane or a mixture thereof.

Preferably, the absorbance is tested at a wavelength of 200 nm to 500 nm. More preferably, the absorbance is tested at a wavelength of 290 nm to 500 nm.

Preferably, the calibration curve is corrected by linear regression.

Preferably, the first polycyclic aromatic hydrocarbon includes at least one selected from the group consisting of benzo[a]pyrene, benzo[e]pyrene, benzo[a]anthracene, benzo[b]fluoranthene, benzo[j]fluoranthene, benzo[k]fluoranthene, chrysene, dibenzo[a,h]anthracene, benzo[g,h,i]perylene, indeno[1,2,3-cd]pyrene, anthracene, fluoranthene, phenanthrene, pyrene, naphthalene, acenaphthylene, acenaphthene, fluorine, 5-methylchrysene, perylene and benzo[ghi]fluoranthene.

Preferably, the calibration curve takes the absorbance of the first polycyclic aromatic hydrocarbon as the data on the vertical axis and the content of the first polycyclic aromatic hydrocarbon as the data on the horizontal axis.

Preferably, the regression curve is corrected linearly.

Preferably, the polycyclic aromatic hydrocarbon includes at least two selected from the group consisting of benzo[a]pyrene, benzo[e]pyrene, benzo[a]anthracene, benzo[b]fluoranthene, benzo[j]fluoranthene, benzo[k]fluoranthene, chrysene, dibenzo[a,h]anthracene, benzo[g,h,i]perylene, indeno[1,2,3-cd]pyrene, anthracene, fluoranthene, phenanthrene, pyrene, naphthalene, acenaphthylene, acenaphthene, fluorine, 5-methylchrysene, perylene and benzo[ghi]fluoranthene.

Preferably, the preparation method of the regression curve includes the following steps: collecting measurement results of carbon black, in which the measurement results include the content of the first polycyclic aromatic hydrocarbon in the carbon black and the content of the polycyclic aromatic hydrocarbon in the carbon black; and performing regression analysis on the measurement results.

The present invention uses a more popular ultraviolet-visible spectrometer to measure the content of PAHs in carbon black, which can eliminate the time for sending for measurement and greatly reduce the measurement time.

DETAILED DESCRIPTION OF THE EMBODIMENTS

Figure 1:
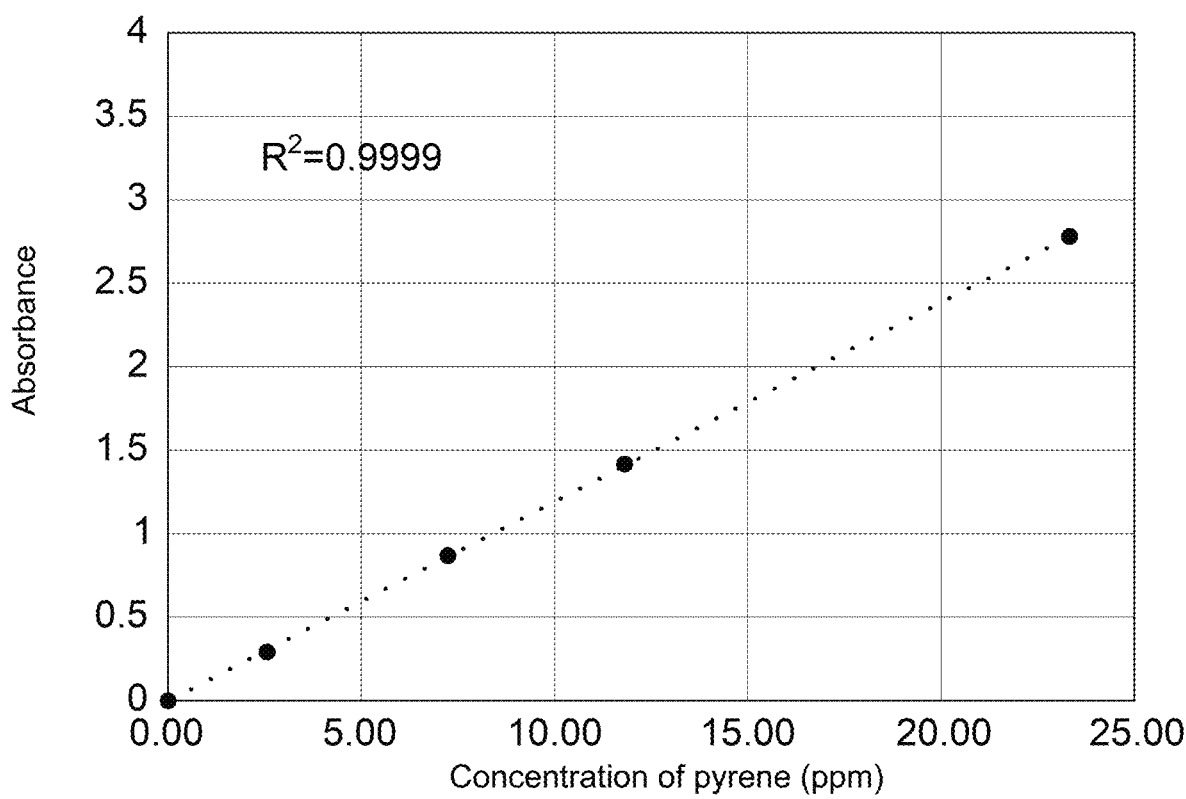
FIG. 1 is a graph showing the relationship between the absorbance of a plurality of standard solutions and the concentration of pyrene contained in the plurality of standard solutions.

The 18 PAHs in the present invention refer to the 18 polycyclic aromatic hydrocarbons listed in Table 1:

TABLE 1

| No. | Name | CAS No. |
| --- | --- | --- |
| 1 | Benzo[a]pyrene | 50-32-8 |
| 2 | Benzo[e]pyrene | 192-97-2 |
| 3 | Benzo[a]anthracene | 56-55-3 |
| 4 | Benzo[b]fluoranthene | 205-99-2 |
| 5 | Benzo[j]fluoranthene | 205-8-23 |
| 6 | Benzo[k]fluoranthene | 207-08-9 |
| 7 | Chrysene | 218-01-9 |
| 8 | Dibenzo[a,h]anthracene | 53-70-3 |
| 9 | Benzo[g,h,i]perylene | 191-24-2 |
| 10 | Indeno[1,2,3-cd]pyrene | 193-39-5 |
| 11 | Anthracene | 120-12-7 |
| 12 | Fluoranthene | 206-44-0 |
| 13 | Phenanthrene | 85-01-8 |
| 14 | Pyrene | 129-00-0 |
| 15 | Naphthalene | 91-20-3 |
| 16 | Acenaphthylene | 208-96-8 |
| 17 | Acenaphthene | 83-32-9 |
| 18 | Fluorene | 86-73-7 |

The 15 PAHs in the present invention refer to 15 kinds of polycyclic aromatic hydrocarbons, which are the compounds numbered 1 to 15 in Table 1 above.

In the present invention, if the terms "first" and "second" are used to describe an ingredient, the ingredient is not restricted by the terms, and the terms are mainly used to distinguish one ingredient from another.

The method for measuring a content of a polycyclic aromatic hydrocarbon in carbon black provided by the present invention includes the following steps: extracting a carbon black to be measured with an organic solvent to obtain a sample to be tested; testing the sample to be tested by ultraviolet-visible spectrometer to obtain an absorbance; and using the absorbance and a calibration curve to obtain a content of a polycyclic aromatic hydrocarbon in the sample to be tested, wherein the calibration curve shows a relationship between the absorbance of the polycyclic aromatic hydrocarbon and the content of the polycyclic aromatic hydrocarbon.

The present invention further provides a method for measuring a content of a polycyclic aromatic hydrocarbon in carbon black, which comprises the following steps: extracting a carbon black to be measured using an organic solvent to obtain a sample to be tested; testing the sample to be tested by ultraviolet-visible spectrometer to obtain an absorbance; using the absorbance and a calibration curve to obtain a content of a first polycyclic aromatic hydrocarbon in the sample to be tested, wherein the calibration curve shows a relationship between the absorbance of the first polycyclic aromatic hydrocarbon and the content of the first polycyclic aromatic hydrocarbon; and using the content of the first polycyclic aromatic hydrocarbon and a regression curve to obtain a content of a polycyclic aromatic hydrocarbon in the sample to be tested, wherein the first polycyclic aromatic hydrocarbon is a part of the polycyclic aromatic hydrocarbon, and the regression curve shows a relationship between the content of the first polycyclic aromatic hydrocarbon and the content of the polycyclic aromatic hydrocarbon.

In the present invention, the carbon black to be measured may be ASTM carbon black, but is not limited thereto. Examples of ASTM carbon black include but are not limited to: N110, N220, N234, N326, N330, N339, N550, N660 and N774.

In the present invention, the organic solvent is preferably one that can dissolve polycyclic aromatic hydrocarbons, more preferably one that can dissolve 18 PAHs, and particularly preferably one that can dissolve 15 PAHs. Examples of the organic solvent include but are not limited to toluene, cyclohexane or a mixture thereof. Since toluene has better solubility for polycyclic aromatic hydrocarbons, it is preferred. In the present invention, the term "soluble" preferably means that the solubility of the organic solvent for polycyclic aromatic hydrocarbons is ≥1000 mg/kg.

In a preferred embodiment, the carbon black to be tested and the organic solvent are mixed in a ratio of 1:10 to 1:40 for extraction.

In the present invention, the absorbance is preferably measured at a wavelength of 200 nm to 500 nm. The absorbance is preferably measured at the absorption wavelength of the type of polycyclic aromatic hydrocarbon (including the first polycyclic aromatic hydrocarbon) to be measured. Examples of the absorption wavelength include, but are not limited to, an integer between 290-500 nm (for example: 300-430 nm), such as: 308, 322, 338, 342, or 425 nm.

In the present invention, the calibration curve can be prepared in accordance with the method described in the amended "Environmental Inspection Calibration Curve Preparation and Verification Guidelines" issued in Inspection No. 0930072069C of Environmental Protection Administration, Executive Yuan on Oct. 4, 2004.

In the present invention, examples of the polycyclic aromatic hydrocarbon used to prepare the calibration curve or the first polycyclic aromatic hydrocarbon used to prepare the calibration curve may be benzo[a]pyrene, benzo[e]pyrene, benzo[a]anthracene, benzo[b]fluoranthene, benzo[j]fluoranthene, benzo[k]fluoranthene, chrysene, dibenzo[a,h]anthracene, benzo[g,h,i]perylene, indeno[1,2,3-cd]pyrene, anthracene, fluoranthene, phenanthrene, pyrene, naphthalene, acenaphthylene, acenaphthene, fluorene, 5-methylchrysene, perylene or benzo[ghi]fluoranthene. In some embodiment, the polycyclic aromatic hydrocarbon or the first polycyclic aromatic hydrocarbon is used alone. In some embodiments, the polycyclic aromatic hydrocarbon or the first polycyclic aromatic hydrocarbon is used in combination of two or more types (such as more than three or more than four types). Since the first polycyclic aromatic hydrocarbon is a part of the polycyclic aromatic hydrocarbon (that is, the polycyclic aromatic hydrocarbon contains the first polycyclic aromatic hydrocarbon), the first polycyclic aromatic hydrocarbon can be used in the polycyclic aromatic hydrocarbon as an internal standard. In a preferred embodiment, the content of the first polycyclic aromatic hydrocarbon is preferably highly positively correlated with the content of the polycyclic aromatic hydrocarbon, in which the highly positively correlated relationship refers to taking the content of the polycyclic aromatic hydrocarbon as data on the vertical axis, performing linear regression with the content of the first polycyclic aromatic hydrocarbon as data on the horizontal axis, and obtaining a regression coefficient ($R^2$) of above 0.95 by the ordinary least square method. The regression coefficient is preferably above 0.97, and particularly preferably above 0.99.

The following illustrates the preparation method of the calibration curve. The method for preparing the calibration curve includes the following steps: preparing a plurality of (preferably three or more, more preferably four or more, particularly preferably five or more) standard solutions containing the polycyclic aromatic hydrocarbon (for example, the first polycyclic aromatic hydrocarbon), in which the concentration of the plurality of standard solutions is different from each other; and measuring the plurality of standard solutions using the ultraviolet-visible spectrometer to obtain the relationship curve (i.e., the calibration curve) of the absorbance of the plurality of standard solutions (data on the vertical axis) with respect to the concentration of the polycyclic aromatic hydrocarbon contained in the plurality of standard solutions (data on the horizontal axis).

In some embodiments, the standard solution is obtained by dissolving the polycyclic aromatic hydrocarbon (such as the first polycyclic aromatic hydrocarbon) in the organic solvent (such as toluene).

The calibration curve of the present invention can be corrected in, for example, a linear mode or a nonlinear mode. Preferably, the calibration curve is corrected in a linear mode. More preferably, the calibration curve is corrected by simple linear regression. The calibration may be performed by a computer program (such as Microsoft Excel).

In a preferred embodiment, the method for preparing the regression curve includes the following steps: collecting measurement results of carbon black, the measurement results including the content of the first polycyclic aromatic hydrocarbon in the carbon black and the content of the polycyclic aromatic hydrocarbon in the carbon black; and performing regression analysis of the measurement results. The regression curve can be linear or non-linear. The regression analysis is preferably simple linear regression. The regression curve preferably takes the content of the polycyclic aromatic hydrocarbon as the data on the vertical axis and the content of the first polycyclic aromatic hydrocarbon as the data on the horizontal axis. The regression analysis may be performed by a computer program (such as Microsoft Excel).

In a preferred embodiment, the first polycyclic aromatic hydrocarbon is a single polycyclic aromatic hydrocarbon, so as to avoid errors caused by excessive variation.

In a preferred embodiment, the method for measuring the content of the polycyclic aromatic hydrocarbon in carbon black is used to measure the total content of 18 PAHs in carbon black. In another preferred embodiment, the method for measuring the content of the polycyclic aromatic hydrocarbon in carbon black is used to measure the total content of 15 PAHs in carbon black.

In some embodiments, the measurement result is the test report of 18 PAHs or 15 PAHs in carbon black with GC-MS by SGS or National Notary Inspection Co., Ltd., and this report is used as the database for regression analysis. The test report can be obtained according to AfPS GS 2014:01 or AfPS GS 2019:01 detection method.

The following examples are used to further illustrate the present invention, but they are not used to limit the scope of the present invention. All the changes and modifications made by people having ordinary skill in the art without departing from the spirit of the present invention fall within the scope of the present invention.

EXAMPLES

Preparation of the Samples to be Tested:

2 grams of ASTM N326 carbon black to be measured were weighted, and 20 mL of toluene was added thereto (that is, the ratio of carbon black to organic solvent is 1:10). Afterwards, extraction with ultrasonic vibration was performed for 1 hour at room temperature, followed by filtering to obtain the sample solution to be tested. The sample solution to be tested was analyzed with an ultraviolet-visible spectrometer to obtain its absorbance.

The samples to be tested were prepared with ASTM N200 and ASTM N550 carbon black as the carbon black to be measured, and the preparation method was the same as above.

Preparation of Calibration Curve (Using Pyrene as the First Polycyclic Aromatic Hydrocarbon):

0, 0.25, 0.72, 1.18 and 2.34 mg of pyrene were weighted and dissolved in 100 g of toluene respectively to obtain standard solutions with concentrations of 0, 2.5, 7.2, 11.8, and 23.4 ppm. These standard solutions were analyzed with an ultraviolet-visible spectrometer. The operation steps are as what follows: (1) using the full-spectrum scanning function of the ultraviolet-visible spectrometer; (2) setting the scanning range to 290~500 nm; (3) setting the sampling interval to ≤1 nm; (4) setting the scanning rate to ≤5 nm/s; (5) setting the slit width to 5 nm; (6) after baseline correction of Blank Cell (here, using organic solvent (pure toluene) as the background value), standard solutions with different concentrations were put in sequence to perform full-spectrum scanning; (6) recording the absorbance values of each standard solution at 308 nm, 322 nm, 338 nm and 342 nm; and (7) obtaining the calibration curve with Microsoft Excel from the collected absorbance data for the standard solutions with different concentrations. The analysis result is shown in FIG. 1. The absorption value is taken from the absorption value at 322 nm as an example. The regression coefficient ($R^2$) of the calibration curve is 0.9999.

Figure 2:
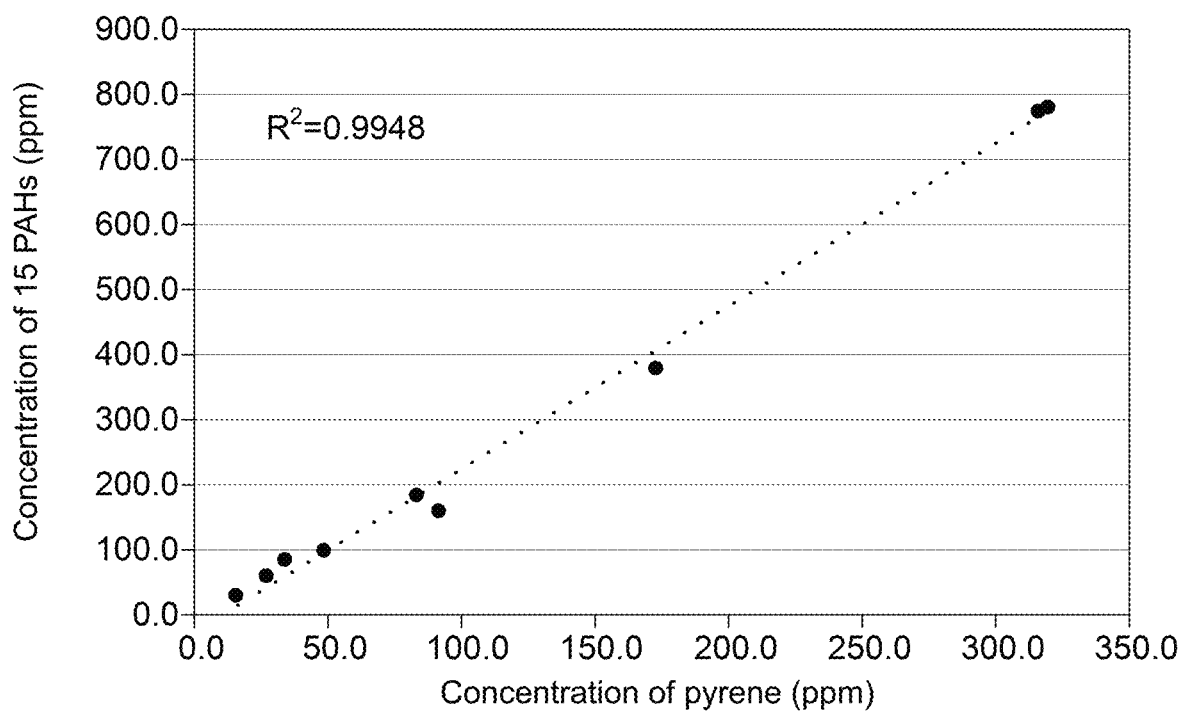
FIG. 2 is a regression curve showing the relationship between the content of pyrene and the content of 15 PAHs.

Preparation of Regression Curve:

The known (i.e., existing) test results were collected as the database for regression analysis. The test results are obtained with GC-MS in accordance with AfPS GS 2019:01 method by third party (for example, National Notarization Inspection Co., Ltd.) on the different batches of ASTM N326 carbon black products, different batches of ASTM N200 carbon black products and different batches of ASTM N550 carbon black products of CSRC. The test result reveals the content of each polycyclic aromatic hydrocarbon in 15 PAHs. Therefore, the total content of 15 PAHs can also be known from the test results. From the known test results, classification was performed according to carbon black grades, the test results of the first polycyclic aromatic hydrocarbons (pyrene) and 15 PAHs in each grade were collected, and regression analysis (simple linear regression) was performed on the test results. The result is shown in FIG. 2. FIG. 2 shows a regression curve (having a regression coefficient $R^2$ of 0.9948), which shows the relationship between the content of pyrene and 15 PAHs. The value is collected from a third party's GC-MS test report on ASTM N326 carbon black.

Table 2 shows the test results of the absorbance of the above-mentioned samples to be tested, the concentration of the first polycyclic aromatic hydrocarbon (pyrene) calculated by the equation obtained from the simple linear regression of the calibration curve using the absorbance, the concentration of 15 PAHs calculated by the equation obtained from the regression analysis using the concentration of the first polycyclic aromatic hydrocarbon and the third party inspection report data.

TABLE 2

| carbon black grade | National Notarization Inspection Report | | The measurement method of the present invention | | |
| --- | --- | --- | --- | --- | --- |
| | Pyrene (ppm) | 15 PAHs (ppm) | absorbance of the sample to be tested | Pyrene (ppm) | 15 PAHs (ppm) |
| N326 | 28.50 | 60.50 | 3.360 | 28.29 | 63.71 |
| N220 | 0.60 | 6.80 | 0.158 | 1.27 | 6.09 |
| N550 | Not detected | 1.30 | 0.155 | 1.24 | 3.06 |

From the above experimental results, it can be seen that this method only takes 1 to 1.5 hours (including the preparation of the sample to be tested) to estimate the PAHs content (for example, the total content of 15 PAHs), so it can achieve rapid screening of carbon black that meets the PAHs content required by laws and regulations (for example, carbon black containing less than 50 ppm PAHs or carbon black containing less than 10 ppm PAHs), thereby effectively monitoring the PAHs content of carbon black on the production line.

It can be seen from the above that the present invention uses a more popular ultraviolet-visible spectrometer to measure the content of polycyclic aromatic hydrocarbons in carbon black, which can eliminate the time for sending for measurement and greatly reduce the measurement time. Moreover, compared with GC-MS, the ultraviolet-visible spectrometer has the advantages of easy operation, simple equipment maintenance, and low equipment maintenance cost. Therefore, the measurement method of the present invention can greatly reduce the cost.

The above are only the preferred embodiments of the present invention and are not intended to limit the present invention. It should be noted that for those of ordinary skill in the art, several improvements and modifications can also be made without departing from the technical principle of the present invention and should also be regarded as the protection scope of the present invention.

What is claimed is:

1. A method for measuring a content of a polycyclic aromatic hydrocarbon in a carbon black, consisting of the following steps:
   extracting a carbon black to be measured using an organic solvent to obtain a sample to be tested; testing the sample to be tested by an ultraviolet-visible spectrometer to obtain an absorbance measurement of the sample; and using the obtained absorbance measurement and a calibration curve to obtain a content of a polycyclic aromatic hydrocarbon in the sample to be tested, wherein the calibration curve illustrates a relationship between the absorbance measurement of the polycyclic aromatic hydrocarbon and the content of the polycyclic aromatic hydrocarbon, wherein the polycyclic aromatic hydrocarbon is soluble in the organic solvent, wherein the calibration curve is corrected by linear regression; and wherein the calibration curve takes the absorbance measurement of the polycyclic aromatic hydrocarbon as data on a vertical axis and the content of the polycyclic aromatic hydrocarbon as data on a horizontal axis.

2. The method of claim 1, wherein the organic solvent is toluene, cyclohexane or a mixture thereof.

3. The method of claim 1, wherein the absorbance is tested at a wavelength of 200 nm to 500 nm.

4. The method of claim 3, wherein the absorbance is tested at a wavelength of 290 nm to 500 nm.

5. The method of claim 1, wherein the polycyclic aromatic hydrocarbon includes at least one selected from the group consisting of benzo[a]pyrene, benzo[e]pyrene, benzo[a]anthracene, benzo[b]fluoranthene, benzo[j]fluoranthene, benzo[k]fluoranthene, chrysene, dibenzo[a,h]anthracene, benzo[g,h,i]perylene, indeno[1,2,3-cd]pyrene, anthracene, fluoranthene, phenanthrene, pyrene, naphthalene, acenaphthylene, acenaphthene, fluorine, 5-methylchrysene, perylene and benzo[ghi]fluoranthene.

6. A method for measuring a content of a polycyclic aromatic hydrocarbon in carbon black, comprising the following steps:
   extracting a carbon black to be measured using an organic solvent to obtain a sample to be tested; testing the sample to be tested by an ultraviolet-visible spectrometer to obtain an absorbance measurement of the sample; using the obtained absorbance measurement and a calibration curve to obtain a content of a first polycyclic aromatic hydrocarbon in the sample to be tested, wherein the calibration curve shows a relationship between the absorbance of the first polycyclic aromatic hydrocarbon and the content of the first polycyclic aromatic hydrocarbon; and using the content of the first polycyclic aromatic hydrocarbon and a regression curve to obtain a content of a polycyclic aromatic hydrocarbon in the sample to be tested, wherein the first polycyclic aromatic hydrocarbon is a part of the polycyclic aromatic hydrocarbon, and the regression curve illustrates a relationship between the content of the first polycyclic aromatic hydrocarbon and the content of the polycyclic aromatic hydrocarbon, wherein the first polycyclic aromatic hydrocarbon and the polycyclic aromatic hydrocarbon are soluble in the organic solvent, wherein the calibration curve takes the absorbance measurement of the first polycyclic aromatic hydrocarbon as data on a vertical axis and the content of the first polycyclic aromatic hydrocarbon as data on a horizontal axis; wherein the regression curve is corrected linearly; and wherein the regression curve takes the content of the polycyclic aromatic hydrocarbon as the data on the vertical axis and the content of the first polycyclic aromatic hydrocarbon as the data on the horizontal axis.

7. The method of claim 6, wherein the organic solvent is toluene, cyclohexane or a mixture thereof.

8. The method of claim 6, wherein the absorbance is tested at a wavelength of 200 nm to 500 nm.

9. The method of claim 8, wherein the absorbance is tested at a wavelength of 290 nm to 500 nm.

10. The method of claim 6, wherein the calibration curve is corrected by linear regression.

11. The method of claim 6, wherein the first polycyclic aromatic hydrocarbon includes at least one selected from the group consisting of benzo[a]pyrene, benzo[e]pyrene, benzo[a]anthracene, benzo[b]fluoranthene, benzo[j]fluoranthene, benzo[k]fluoranthene, chrysene, dibenzo[a,h]anthracene, benzo[g,h,i]perylene, indeno[1,2,3-cd]pyrene, anthracene, fluoranthene, phenanthrene, pyrene, naphthalene, acenaphthylene, acenaphthene, fluorine, 5-methylchrysene, perylene and benzo[ghi]fluoranthene.

12. The method of claim 6, wherein the polycyclic aromatic hydrocarbon includes at least two selected from the group consisting of benzo[a]pyrene, benzo[e]pyrene, benzo[a]anthracene, benzo[b]fluoranthene, benzo[j]fluoranthene, benzo[k]fluoranthene, chrysene, dibenzo[a,h]anthracene, benzo[g,h,i]perylene, indeno[1,2,3-cd]pyrene, anthracene, fluoranthene, phenanthrene, pyrene, naphthalene, acenaphthylene, acenaphthene, fluorine, 5-methylchrysene, perylene and benzo[ghi]fluoranthene.

13. The method of claim 6, wherein a preparation method of the regression curve includes the following steps:
   collecting measurement results of carbon black, the measurement results include the content of the first polycyclic aromatic hydrocarbon in the carbon black and the content of the polycyclic aromatic hydrocarbon in the carbon black; and
   performing regression analysis on the measurement results.

14. The method of claim 6, wherein the content of the polycyclic aromatic hydrocarbon in the carbon black is able to be rapidly determined.

* * * * *